(12) United States Patent
Akutsu et al.

(10) Patent No.: US 9,734,985 B2
(45) Date of Patent: Aug. 15, 2017

(54) ANALYTICAL APPARATUS, SAMPLE HOLDER AND ANALYTICAL METHOD

(71) Applicant: Kabushiki Kaisha Toshiba, Minato-ku (JP)

(72) Inventors: Haruko Akutsu, Yokosuka (JP); Makiko Katano, Hiratsuka (JP); Akira Kuramoto, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/045,624

(22) Filed: Feb. 17, 2016

(65) Prior Publication Data

US 2017/0004954 A1   Jan. 5, 2017

Related U.S. Application Data

(60) Provisional application No. 62/187,433, filed on Jul. 1, 2015.

(51) Int. Cl.
| | | |
|---|---|---|
| *G21K 5/08* | (2006.01) | |
| *H01J 37/28* | (2006.01) | |
| *H01J 37/248* | (2006.01) | |
| *H01J 37/22* | (2006.01) | |
| *H01J 37/244* | (2006.01) | |

(52) U.S. Cl.
CPC .......... *H01J 37/248* (2013.01); *H01J 37/222* (2013.01); *H01J 37/244* (2013.01); *H01J 37/28* (2013.01); *H01J 2237/2007* (2013.01); *H01J 2237/2801* (2013.01)

(58) Field of Classification Search
USPC ... 250/306, 307, 310, 396 R, 442.11, 453.11
See application file for complete search history.

(56) References Cited

U.S. PATENT DOCUMENTS

| | | | | |
|---|---|---|---|---|
| 4,891,516 A | * | 1/1990 | Balter | H01J 37/20 250/310 |
| 2011/0103681 A1 | | 5/2011 | Kelly | |
| 2012/0080596 A1 | | 4/2012 | Vandervorst | |
| 2012/0205538 A1 | | 8/2012 | Schertel | |
| 2014/0070110 A1 | * | 3/2014 | Kitamoto | G01N 23/00 250/393 |
| 2015/0348743 A1 | * | 12/2015 | Hanada | H01J 37/20 250/442.11 |
| 2016/0035535 A1 | * | 2/2016 | Shimakura | H01J 37/20 250/442.11 |

FOREIGN PATENT DOCUMENTS

| | | |
|---|---|---|
| JP | 2009-110713 | 5/2009 |
| JP | 2012-73242 | 4/2012 |
| JP | 2012-146659 | 8/2012 |

* cited by examiner

*Primary Examiner* — Bernard Souw
(74) *Attorney, Agent, or Firm* — Oblon, McClelland, Maier & Neustadt, L.L.P.

(57) ABSTRACT

In accordance with an embodiment, an analytical apparatus includes a member, a voltage source connected to the member and a detecting section. The member has an inserting portion into which a sample holder supporting a sample is insertable and whose shape corresponds to a shape of the sample holder. The detecting section is configured to detect a substance to be emitted from the sample by field evaporation. The shape of the inserting portion in a cross section of a direction perpendicular to an inserting direction of the sample holder is a shape excluding a perfect circle.

14 Claims, 11 Drawing Sheets

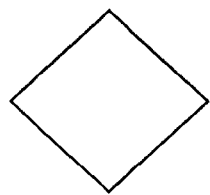
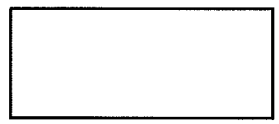
FIG.6A      FIG.6B
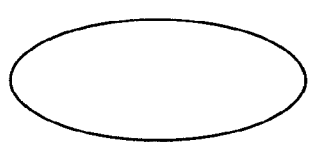
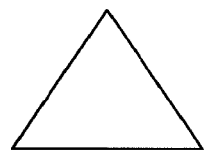
FIG.6C      FIG.6D
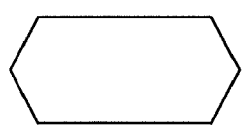
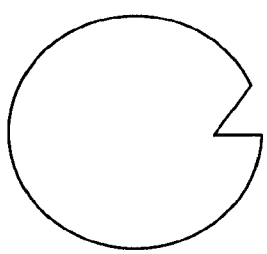
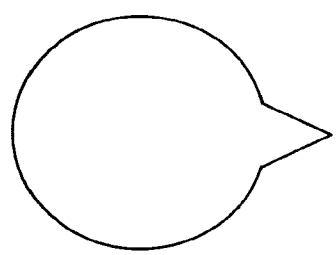
FIG.6E      FIG.6F      FIG.6G

ANALYTICAL APPARATUS, SAMPLE HOLDER AND ANALYTICAL METHOD

CROSS REFERENCE TO RELATED APPLICATIONS

This application is based upon and claims the benefit of U.S. provisional Application No. 62/187,433, filed on Jul. 1, 2015, the entire contents of which are incorporated herein by reference.

FIELD

Embodiments described herein relate generally to an analytical apparatus, a sample holder and an analytical method.

BACKGROUND

In accordance with miniaturization of electronic devices or high densification of magnetic recording, there are required technologies of investigating structures or properties of more microscopic areas.

In recent years, as a local analytical technology at an atom level, an atom probe electric field ion microscope apparatus (hereinafter simply referred to as "the AP apparatus") has attracted attention. The AP apparatus applies a high voltage of an order of several kV to 10 kV to a sample shaped in the form of a needle, to cause field evaporation of atoms themselves in a tip portion of the sample by a high electric field generated at the tip, and then performs mass spectrometry of ions generated by the field evaporation to investigate a structure of the tip portion of the sample.

In recent years, a technology called as an atom probe tomography (APT) has appeared due to improvement of a detector portion. The ATP can simultaneously measure positions and species of atoms of a sample tip, and hence, the structure of the sample tip can three-dimensionally be reconstituted with an atomic resolution. In this point, this kind of probe has features which are not seen in other local analytical apparatuses, thus attracting attention.

On the other hand, there is also an apparatus which irradiates the sample with an electron beam to detect a secondary electron or a transmission electron, thereby inspecting a fine structure of the sample. An example of the apparatus which detects the secondary electron is a scanning electron microscope (SEM), and examples of the apparatus which detects the transmission electron include a transmission electron microscope (TEM) and a scanning transmission electron microscope (STEM).

For dimension measurement of a high accuracy of 1 nm level which is required for element miniaturization, the SEM is poor in a spatial resolution. The TEM and STEM employ a transmitting method and therefore have a higher resolution than the SEM, and hence, these microscopes have been used in a case where the finer and more accurate dimension measurement is required.

Thus, there begins to be required a technology of further improving an analysis accuracy by a composite analysis in which an analysis by the AP apparatus and an analysis by the TEM or the like using the electron beam are combined.

When such a composite analysis is performed, the same observation area has to be found from respective data.

However, for example, in the case of observation of a grain boundary having a size of 10 nm or less, all crystal grains have the same shape and size, and hence, there is the problem that it is difficult to specify the crystal grain which is being observed.

BRIEF DESCRIPTION OF THE DRAWINGS

In the accompanying drawings:

FIG. 6A to FIG. 6G are views showing several examples of a shape of a hole disposed in each base;

DETAILED DESCRIPTION

In accordance with an embodiment, an analytical apparatus includes a member, a voltage source connected to the member and a detecting section. The member has an inserting portion into which a sample holder supporting a sample is insertable and whose shape corresponds to a shape of the sample holder. The detecting section is configured to detect a substance to be emitted from the sample by field evaporation. The shape of the inserting portion in a cross section of a direction perpendicular to an inserting direction of the sample holder is a shape excluding a perfect circle.

Embodiments will now be explained with reference to the accompanying drawings. Like components are provided with like reference signs throughout the drawings and repeated descriptions thereof are appropriately omitted. It is to be noted that the accompanying drawings illustrate the invention and assist in the understanding of the illustration and that the shapes, dimensions, and ratios and so on in each of the drawings may be different in some parts from those in an actual apparatus.

Hereinafter, an AP apparatus capable of preparing a three-dimensional atom map will be described as an example of an analytical apparatus, but the present invention is not limited thereto, and needless to say, the present invention is also applicable to an AP apparatus which prepares a two-dimensional atom map. In addition, as an example of an inspection apparatus to specify a crystal grain boundary of a sample, a TEM will be described, but the present invention is not limited to this apparatus, and a similar inspection can be performed even by using a STEM or a SEM.

Figure 1:
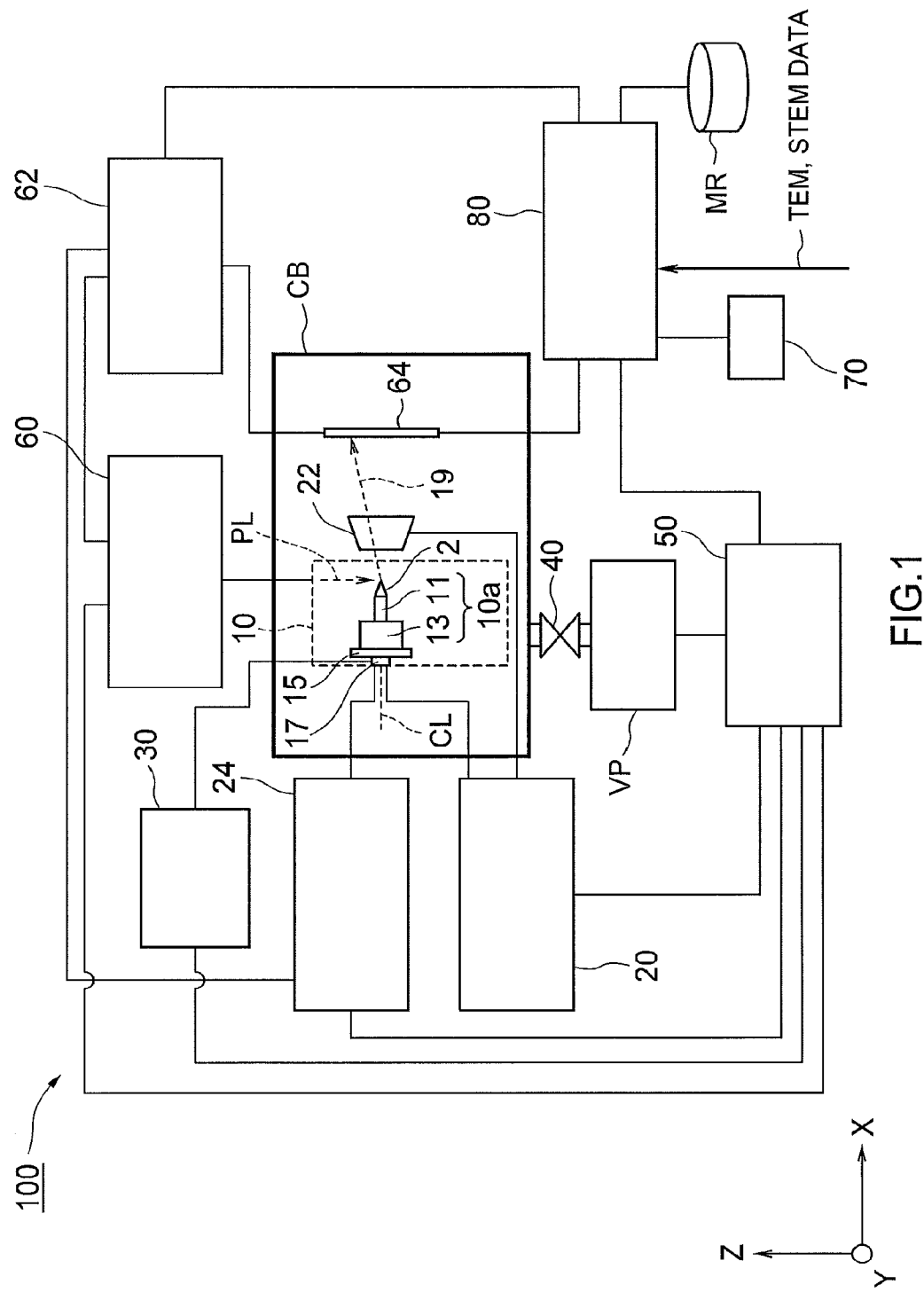
FIG. 1 is one example of a block diagram showing a schematic constitution of an analytical apparatus according to one embodiment.

(A) Analytical Apparatus and Sample Holder (1) Schematic Constitution of Analytical Apparatus FIG. 1 is one example of a block diagram showing a schematic constitution of an analytical apparatus according to one embodiment. An analytical apparatus 100 shown in FIG. 1 includes a processing chamber CB, a control computer 50, a high voltage supplying section 20, a pulse voltage supplying section 24, a cooler 30, a pulse laser outputting section 60, a flying time analyzing section 62, a fixing portion 10 housed in the processing chamber CB, a detector 64, an analyzing section 80, and a display section 70.

The processing chamber CB is a chamber made of a metal such as stainless steel (SUS) to form a vacuum in the processing chamber CB, and is connected to a vacuum pump VP via a valve 40.

The fixing portion 10 includes a base 15 and a base position adjusting section 17. The base 15 fixes, to the inside of the processing chamber CB, a sample holder 10a to which a needle-shaped sample 1 whose tip is sharpened is to be connected for local analysis. The base position adjusting section 17 is coupled with the base 15 to regulate a position of the base 15, especially an angle of the base to a plane perpendicular to a virtual line CX1 passing the tip of the needle-shaped sample 1, i.e., an X-Y plane in an orthogonal coordinate system of X-Y-Z shown in FIG. 1 (see FIG. 9A). In the present embodiment, the base 15 corresponds to, for example, a member, and the base position adjusting section 17 corresponds to, for example, a position adjusting section.

Each of the base 15 and the sample holder 10a is made of a conductive material including at least one selected from the group consisting of copper (Cu), aluminum (Al), silver (Ag), gold (Au), nickel (Ni), tungsten (W), molybdenum (Mo), platinum (Pt), brass, stainless steel, and silicon (Si) whose conductivity is improved by doping impurities. Specific shapes and the like of the base 15 and the sample holder 10a will be described later in detail. In the present embodiment, the X-Y plane corresponds to, for example, an arbitrary reference surface.

The control computer 50 is connected to the vacuum pump VP, the high voltage supplying section 20, the pulse voltage supplying section 24, the cooler 30, the pulse laser outputting section 60, the flying time analyzing section 62 and the analyzing section 80, and generates various control signals to control these members.

The high voltage supplying section 20 is connected to the needle-shaped sample 1 via the base 15 and the sample holder 10a, and connected to an electrode 22 interposed between the needle-shaped sample 1 and the detector 64, and supplies a high voltage to generate a positive electric field at the tip of the needle-shaped sample 1. The electrode 22 is connected to the high voltage supplying section 20, generates a local high electric field, and has a function of assisting field evaporation from the surface of the sample. The cooler 30 is connected to the fixing portion 10 to cool the needle-shaped sample 1.

The pulse voltage supplying section 24 generates a pulse voltage, and applies the voltage to the needle-shaped sample 1 via the base 15 and the sample holder 10a. In consequence, atoms of the tip of the needle-shaped sample 1 are ionized (hereinafter, the atoms ionized in this manner will be referred to as "the ionized atoms"), and emitted as ionized atoms 19 toward a detecting surface of the detector 64.

The detector 64 is disposed away from the sample holder 10a to face the tip of the needle-shaped sample 1, and detects the ionized atoms 19 emitted from the needle-shaped sample 1.

The detector 64 is a position sensitive type of detector in the present embodiment, and can measure positions of the reached ionized atoms 19. The measurement result is sent to the analyzing section 80.

The flying time analyzing section 62 is connected to the pulse voltage supplying section 24 and the detector 64, calculates a flying time of the ionized atoms 19 using a control signal for the pulse voltage to be supplied from the pulse voltage supplying section 24 and the detection result sent from the detector 64, and gives the flying time to the analyzing section 80. The analyzing section 80 calculates a position of each ionized atom 19 flied to the detector 64 in a depth direction of the needle-shaped sample 1 ((x) in the coordinate system shown in FIG. 1) from the flying time of the ionized atom 19.

The analyzing section 80 processes a signal concerning a plane position (y, z) of the ionized atom 19 sent from the detector 64 and information concerning the flying time sent from the flying time analyzing section 62 to obtain positional information (y, z, x) of each ionized atom 19 to prepare the three-dimensional atom map (see FIG. 11), thereby storing the map in a memory device MR and displaying the map in the display device 70. In the present embodiment, the three-dimensional atom map corresponds to, for example, a three-dimensional atom probe image.

The analytical apparatus 100 of the present embodiment can perform pulse laser measurement in addition to pulse voltage measurement by the abovementioned pulse voltage application.

Specifically, the analytical apparatus 100 of the present embodiment further includes the pulse laser outputting section 60 which generates a pulse laser PL to irradiate the needle-shaped sample 1 with the laser. The pulse laser outputting section 60 is also connected to the flying time analyzing section 62, and also sends a control signal to generate the pulse laser PL to the flying time analyzing section 62. The flying time analyzing section 62 calculates the flying time of the ionized atom 19 from the control signal sent using the pulse laser outputting section 60 and the detection result from the detector 64 to send the flying time to the analyzing section 80.

Figure 10:
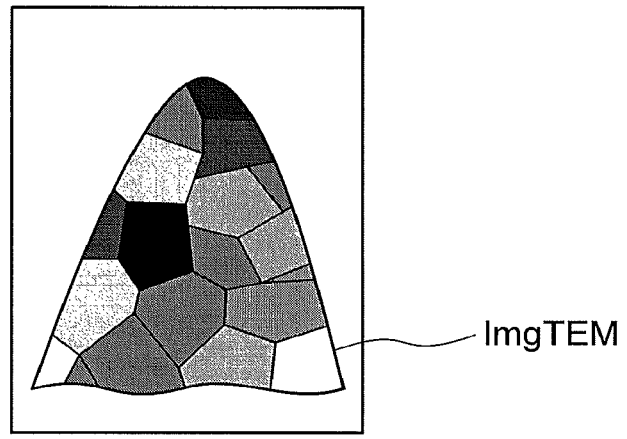
FIG. 10 is one example of a schematic view showing one example of a crystal grain boundary obtained by a TEM inspection as to a needle-shaped sample shown in FIG. 4 and FIG. 5.

In the same manner as in the pulse voltage measurement, the analyzing section 80 processes the signal concerning the plane position (y, z) of the ionized atom 19 which is sent from the detector 64 and the information concerning the flying time which is sent from the flying time analyzing section 62 to obtain the positional information (y, z, x) of each ionized atom 19, thereby preparing the three-dimensional atom map (see FIG. 10).

The analyzing section 80 also associates crystal grain boundary data or the like sent by an external inspection apparatus such as the TEM or the STEM, with the three-dimensional atom map obtained as to the same needle-shaped sample 1, to specify an observation area, and executes analysis to the specified observation area.

Furthermore, the analyzing section 80 uses data of an observation image by an external apparatus such as the TEM or the STEM, to judge whether or not the once prepared three-dimensional atom map obtained as to the same needle-shaped sample 1 is accurate, and when it is judged that the three-dimensional atom map is not accurate, the three-dimensional atom map can more accurately be reconstituted.

It is to be noted that the observation image by the abovementioned external apparatus is not limited to a transmission image, and also includes a diffraction image and an electron back scatter diffraction image, and when the crystal grain boundary data is not required, an energy filter image and a scanning electron microscope image are also included.

(2) Sample Holder

Figure 2:
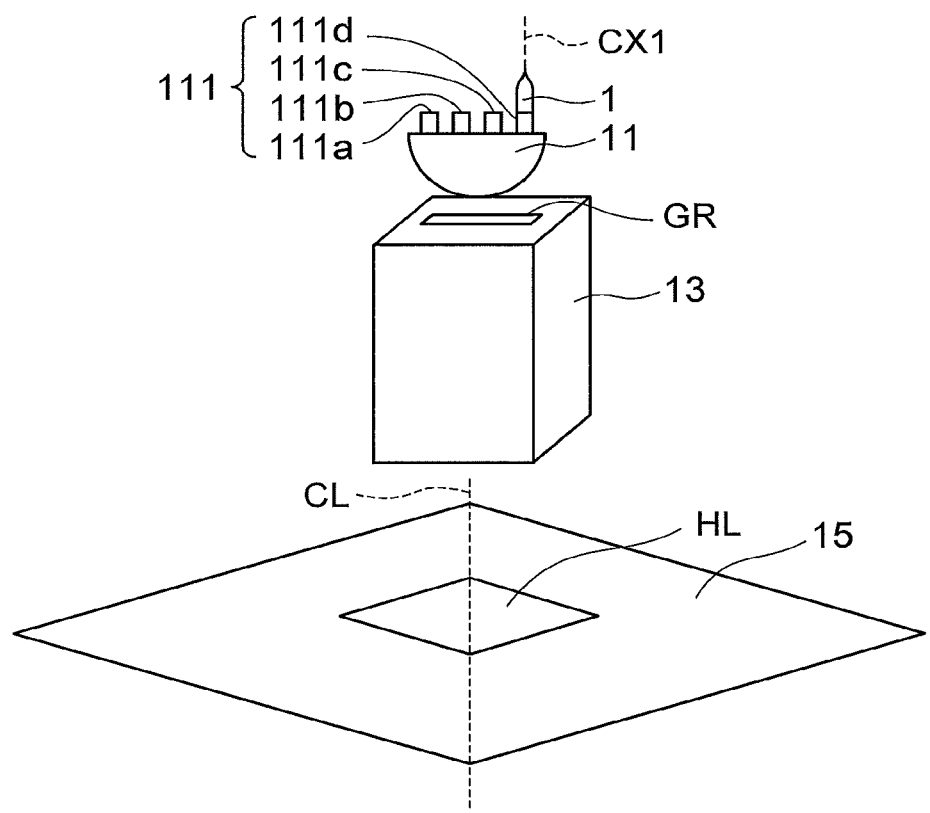
FIG. 2 is one example of an exploded perspective view showing one example of an exploded perspective view of a sample holder together with one example of a base.

FIG. 2 shows one example of an exploded perspective view of the sample holder 10a together with one example of the base 15. The sample holder 10a includes an adapter 13, a sample holding tool 11 and the needle-shaped sample 1.

Of the base 15 shown in FIG. 2, there is disposed a hole HL having a rectangular plane shape seen from an adapter 13 side. In both end portions of the adapter 13, the end portion facing the base 15 has a peripheral edge shape similar to the hole HL of the base 15, whereby the adapter 13 is attached to the base 15 to be inserted and fitted into the hole HL of the base 15. A groove GR is disposed in a top surface of the adapter 13 (the surface on a side opposite to the base 15). In the present embodiment, the end portion of the adapter 13 which faces the base 15 corresponds to, for example, a second end portion.

The sample holding tool 11 is also called as a mesh. In the example shown in FIG. 2, the sample holding tool 11 has a comb teeth shape in which a plurality of projections 111 (111a to 111d) are disposed on a half disc-like main body, and its circular side is attached and fixed to the groove GR of the adapter 13. It is to be noted that the shape of the sample holding tool 11 is not necessarily limited to the example shown in FIG. 2, and various shapes can be selected in accordance with a shape of the adapter, a disposing configuration in the analytical apparatus, or the like.

Figure 3:
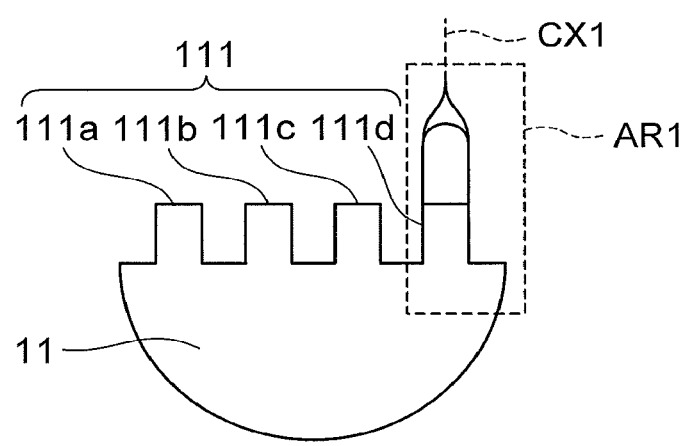
FIG. 3 is one example of an enlarged view of a sample holding tool.

FIG. 3 shows one example of an enlarged view of the sample holding tool 11. As shown in FIG. 3, in the present embodiment, the four projections 111a to 111d are disposed on the sample holding tool 11. Each of the comb teeth-like projections 111 of the sample holding tool 11 is connected to the needle-shaped sample 1. In the present embodiment, each of the teeth-like projections 111 corresponds to, for example, a first end portion.

Figure 4:
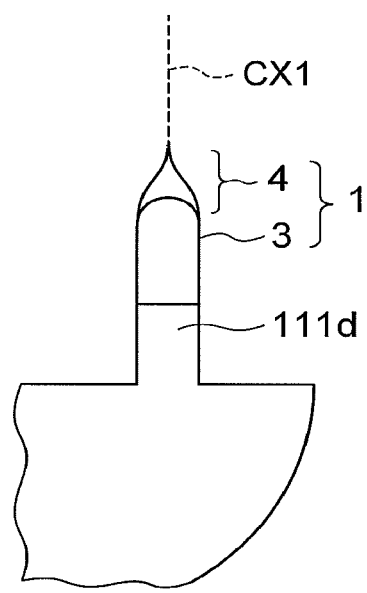
FIG. 4 is one example of an enlarged view of an area specified by a dotted line in FIG. 3.

FIG. 4 is one example of a partial enlarged view of FIG. 3 and shows an enlarged view of an area AR1 specified by a dotted line in FIG. 3.

Figure 5:
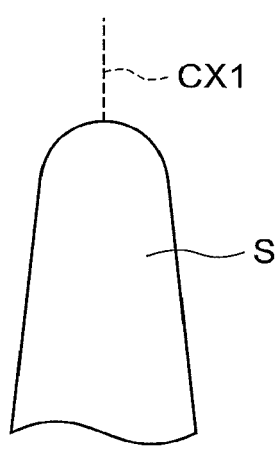
FIG. 5 is a view showing one example of an area to be measured which is disposed in a needle-shaped portion.

The needle-shaped sample 1 includes a columnar portion 3 and a needle-shaped portion 4. In the present embodiment, the columnar portion 3 is connected to the projection 111d to project from the projection 111d. The needle-shaped portion 4 is sharpened to form a conical member from the end portion of the columnar portion 3 on a side opposite to the sample holding tool 11 side toward a direction in which the columnar portion 3 projects, and as shown in FIG. 5, an area S to be measured as an analysis object is disposed in a sharpened tip portion.

FIG. 3 and FIG. 4 show the example where the single needle-shaped sample 1 is only connected to the projection 111d. However, the needle-shaped sample 1 is connectable to each of the other projections 111a to 111c, and the sample holding tool 11 of the present embodiment is configured to analyze the four needle-shaped samples 1 in total. Needless to say, the number of the samples is not limited to four, and it is possible to use the sample holding tool connectable to three or less samples or five or more samples.

It is to be noted that in FIG. 2 to FIG. 5, a dotted line denoted with sign CX1 is a virtual line passing the tip in a direction in which the needle-shaped portion 4 is sharpened (hereinafter referred to as "the axial line CX1").

Returning to FIG. 1, a position of the base 15 is adjusted by the base position adjusting section 17 to fix the base. As described above, the shape of the hole HL of the base 15 in a cross section of a direction perpendicular to an inserting direction of the adapter 13 is rectangular, and hence, once the position of the base 15 is determined, the position of the needle-shaped sample 1 is also determined via the adapter 13 and the sample holding tool 11. As a result, the sample holder 10a is prevented from being rotated around an axial line CL (the line passing the center of the base 15 and extending perpendicularly to the surface of the base 15 which faces the sample holder 10a).

Therefore, as described later in detail, when the same base 15 is used at the same position in both of the analytical apparatus 100 of the present embodiment and another inspection apparatus and when the identical sample holder 10a is shared between these apparatuses, the position of the needle-shaped sample 1 in a rotating direction around the axial line CX1 is not moved (refer to FIG. 9B) but is substantially defined as the same position, and the inspection result obtained by the other inspection apparatus can be utilized as it is in sample analysis in which the three-dimensional atom map is used. This enables an accurate analysis to an element in a fine structure. Here, "substantially" indicates that an error is included up to such an extent that the crystal grain boundary data can be associated with the three-dimensional atom map.

The shape of the hole HL of the base in the cross section in the perpendicular direction to the inserting direction of the adapter 13 is not limited to the rectangular shape, and may be any shape as long as the needle-shaped sample 1 cannot rotate via the adapter 13 and the sample holding tool 11.

FIG. 6A to FIG. 6F show several examples of the shape of the hole HL in the cross section of the perpendicular direction to the inserting direction of the adapter 13. In addition to the rectangular shapes shown in FIG. 6A and FIG. 6B, an elliptic shape of FIG. 6C, or a polygonal shape such as a triangular shape of FIG. 6D or a hexagonal shape of FIG. 6E is usable. A perfect circle itself is not usable, but as shown in, e.g., FIG. 6F and FIG. 6G, a shape including a circular portion may be used as long as a concave portion, a convex portion or the like is disposed, because the needle-shaped sample 1 can be prevented from being rotated around the axial line CL of the base 15. In the present embodiment, the hole HL corresponds to, for example, an inserting portion.

As described above, according to the present embodiment, the sample holder 10a includes the adapter 13 which has the peripheral edge shape corresponding to the shape of the hole of the base 15 and is prevented from being rotated, and the position of the needle-shaped sample 1 is fixed in the rotating direction around the axial line CX1 passing the tip of the sample and extending in the direction in which the needle-shaped sample 1 is sharpened, so that inspection results by a different types of apparatuses can be associated with one another and utilized. In consequence, as described later, when the identical sample holder 10a is used in an electron microscope and an AP apparatus, the observation area can be specified for each crystal.

(B) Analytical Method

Several embodiments of an analytical method of the needle-shaped sample in which the analytical apparatus 100 of the abovementioned embodiment is used will be described with reference to FIG. 7 to FIG. 15.

(1) Embodiment 1

Figure 7:
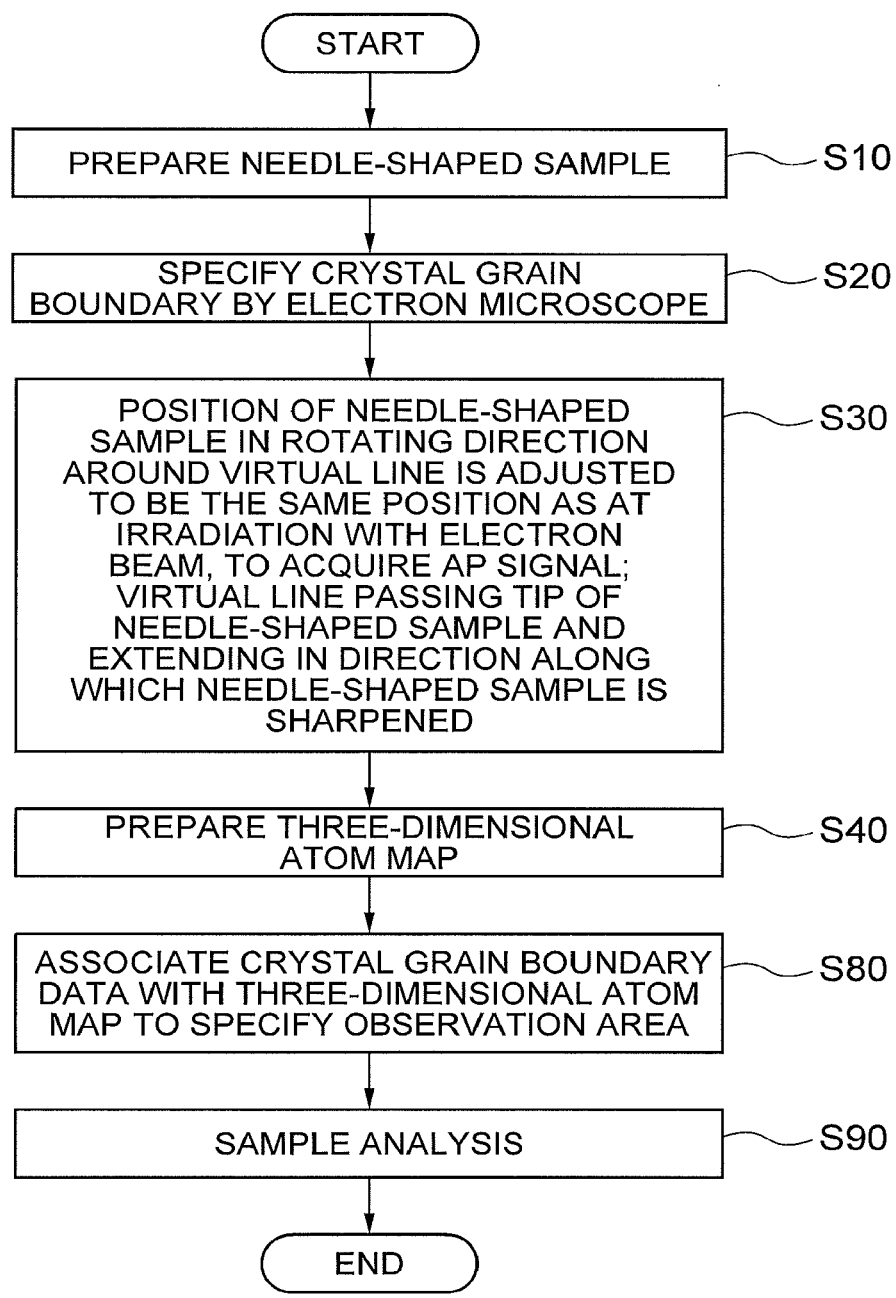
FIG. 7 is a flowchart showing a schematic procedure of an analytical method according to Embodiment 1.

FIG. 7 is a flowchart showing a schematic procedure of an analytical method according to Embodiment 1.

First, a needle-shaped sample is prepared (step S10).

Next, the prepared needle-shaped sample is set to an electron microscope such as a SEM, a TEM or a STEM to irradiate the sample with an electron beam, an electron generated from the needle-shaped sample is detected and an obtained signal is processed to specify a crystal grain boundary of the needle-shaped sample (step S20). It is to be noted that not only a transmission image but also a diffraction image and an electron back scatter diffraction image are usable in specifying the crystal grain boundary.

Subsequently, the identical sample is moved from the electron microscope into an AP apparatus, e.g., the processing chamber CB of the analytical apparatus 100 shown in FIG. 1 and set to the base 15 of the fixing portion 10 to apply a high voltage to the sample, and the ionized atom 19 is detected by the position sensitive type of detector 64 to acquire a signal (hereinafter called "the AP signal") including positional information (y, z, x) of each flied ionized atom (step S30). When the needle-shaped sample is set to the AP apparatus, the position of the needle-shaped sample in the rotating direction around the virtual line passing the tip of the needle-shaped sample and extending in the direction in which the needle-shaped sample 1 is sharpened is substantially defined as the same position as in irradiation with an electron beam EB, i.e., the needle-shaped sample 1 is moved in such a manner that the axial line CX1 is directed in the same azimuth and that the needle-shaped sample 1 does not rotate around the axial line CX1. An adjusting method to prevent the rotation of the needle-shaped sample 1 will specifically be described later.

Here, "substantially" indicates that an error is included to such an extent that crystal grain boundary data can be associated with a three-dimensional atom map, and, for example, when a grain boundary size of an observation object is 5 nm, an error of 1 degree or less is included in substantially the same position, and when the size is 10 nm, an error of 2 degree or less is included in substantially the same position.

Furthermore, the obtained AP signal is processed to prepare the three-dimensional atom map by the analyzing section 80 (step S40). In the present embodiment, the three-dimensional atom map corresponds to, for example, a three-dimensional atom probe image.

Next, the data of the crystal grain boundary specified by inspection with the electron microscope is associated with the three-dimensional atom map by the analyzing section 80, to specify an observation area (step S80).

Finally, analysis of the needle-shaped sample is performed for each specified observation area by the analyzing section 80 (step S90).

The abovementioned steps S20 to S90 will be described in more detail with reference to FIG. 8 to FIG. 11.

(a) Preparation of Needle-Shaped Sample

The needle-shaped sample can be prepared by using an existing technology such as photolithography or a focused ion beam (FIB) to process an analysis object. In the present embodiment, the needle-shaped sample 1 as shown in FIG. 2 to FIG. 5 is prepared.

(b) Acquisition of Crystal Grain Boundary Data of Needle-Shaped Sample

Figure 8:
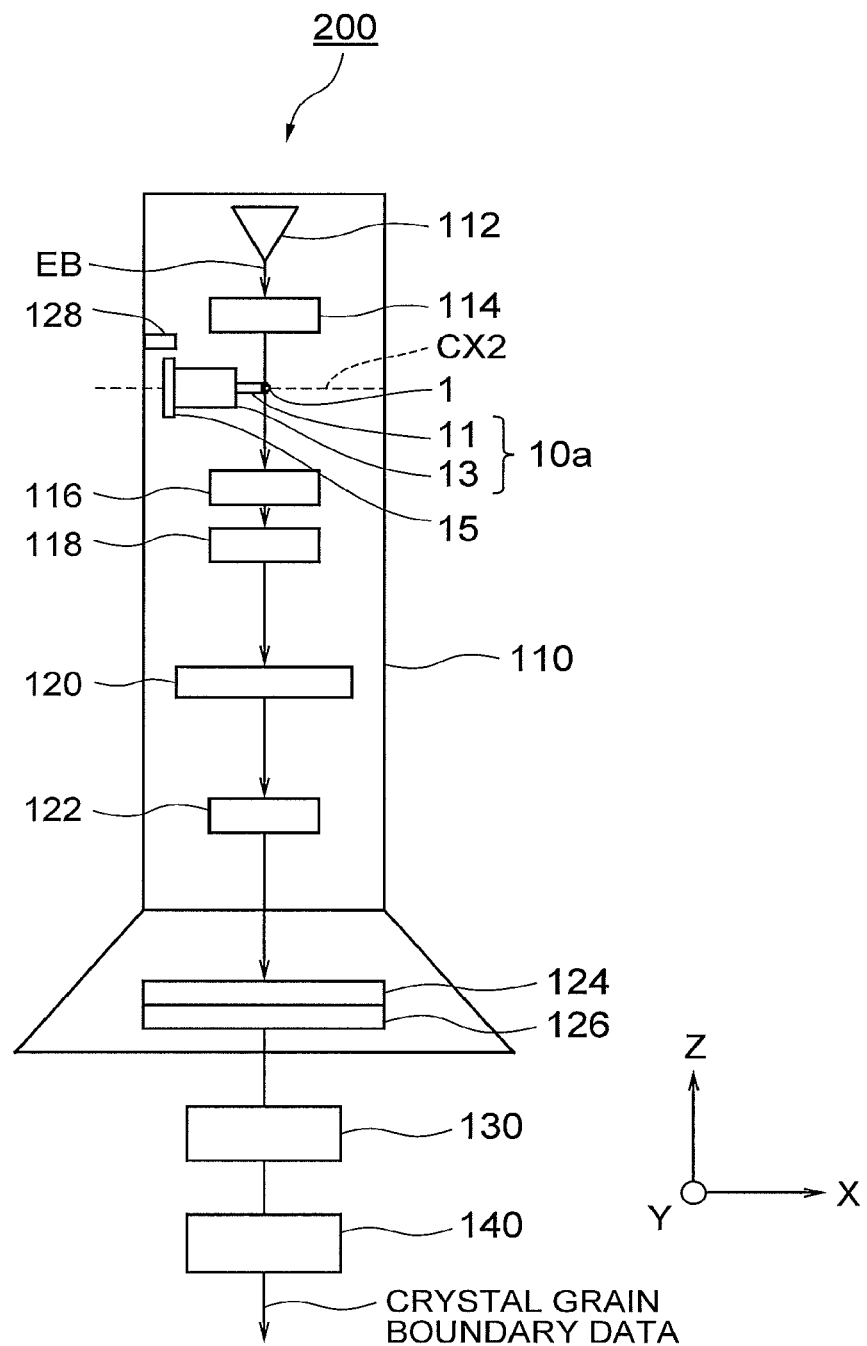
FIG. 8 is one example of a block diagram showing one example of a TEM.

Here, there is described a case where the TEM is used. FIG. 8 is a block diagram showing one example of the TEM.

A TEM 200 shown in FIG. 8 includes a column 110, an image processing section 130, and an analyzing section 140. In the column 110, there are disposed an electron gun 112, a condensing lens 114, a position sensor 128, an objective lens 116, a selected-area aperture plate 118, an intermediate lens 120, a projecting lens 122, a fluorescent plate 124, and an imaging section 126.

First, the needle-shaped sample is set and fixed between the condensing lens 114 and the objective lens 116. In the present embodiment, as the needle-shaped sample, the needle-shaped sample 1 included in the sample holder 10a, such as shown in FIG. 2 to FIG. 5, is used.

As described above, the needle-shaped sample 1 is attached to the base 15 via the sample holding tool 11 and the adapter 13, to be prevented from being rotated around the axial line CX1 shown in FIG. 2 to FIG. 5.

In this state, the sample is irradiated with the electron beam EB from the electron gun 112. The electron beam EB emitted from the electron gun 112 is condensed by the condensing lens 114 to pass the needle-shaped sample 1. After passing the needle-shaped sample 1, the electron beam EB enters into the fluorescent plate 124 through the objective lens 116, the selected-area aperture plate 118, the intermediate lens 120 and the projecting lens 122. In consequence, an electron microscope image of the needle-shaped sample 1 is formed on the fluorescent plate 124.

The imaging section 126 images the electron microscope image of the fluorescent plate 124, and an obtained image signal is sent to the analyzing section 140 via the image processing section 130. The analyzing section 140 processes the image signal to specify the crystal grain boundary in the needle-shaped sample 1. In the present embodiment, the electron microscope image imaged by the imaging section 126 corresponds to, for example, the transmission image, and the image signal outputted from the imaging section 126 corresponds to, for example, a first signal.

FIG. 10 is a schematic view showing one example of the crystal grain boundary obtained by a TEM inspection of the needle-shaped sample 1. As seen from FIG. 10, the crystal grain boundary is specified in a TEM image ImgTEM, and respective areas of crystals are clearly defined.

The crystal grain boundary data specified in this manner is outputted from the analyzing section 140 of the TEM 200 and sent to another inspection apparatus, e.g., the analytical apparatus 100 shown in FIG. 1 through on-line or off-line.

Figure 9A:
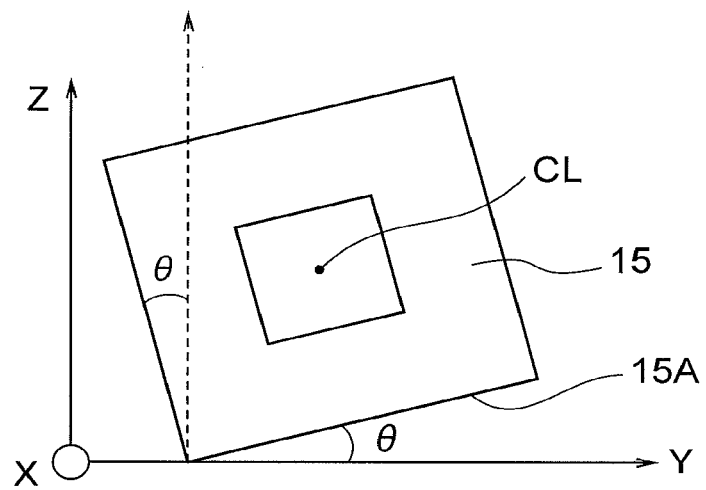
FIG. 9A is one example of a view showing a measurement example of a base position by a position sensor of the TEM shown in FIG. 8.
Figure 9B:
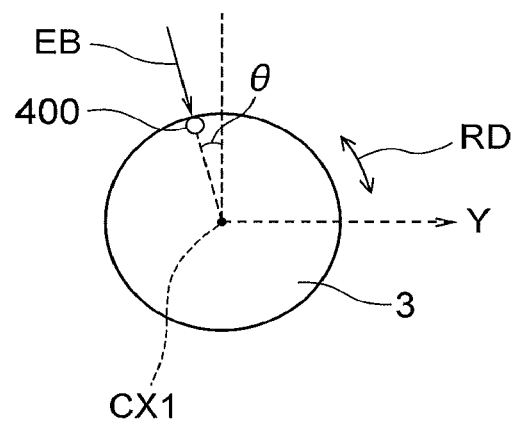
FIG. 9B is a view showing one example of an adjustment result by a base position adjusting section of the analytical apparatus shown in FIG. 1.

In addition, an azimuth of an axial line CX2 (see FIG. 8) of the needle-shaped sample 1 at the time of acquisition of the electron microscope image is measured by the position sensor 128. More specifically, as shown in FIG. 9A, an angle θ between a surface of the base 15, e.g., a surface 15A facing the fluorescent plate 124 and the XY plane is measured by the position sensor 128.

(c) Acquisition of AP Signal and Preparation of Three-Dimensional Atom Map

As preliminary preparation, in accordance with the measurement result of the position sensor 128 of the TEM 200, the position of the base 15 is adjusted by the base position adjusting section 17 in such a manner that an angle between a surface of the base 15 of the analytical apparatus 100 on the side opposite to the pulse laser output side and the XY plane is the same as the angle θ in the TEM 200. However, when information of the angle θ is beforehand known in the TEM 200, the position of the base 15 may be adjusted by the base position adjusting section 17 of the analytical apparatus 100 in accordance with this information, and hence, preprocessing, in which the position sensor 128 is used, is not required.

When the crystal grain boundary data of the needle-shaped sample 1 is obtained by the TEM 200, the sample holder 10*a* is removed from the TEM 200 and set to the base 15 of the analytical apparatus 100 shown in FIG. 1.

At this time, the position of the base 15, especially the angle between the base and the XY plane is already adjusted by the base position adjusting section 17 in such a manner that the angle matches the angle θ in the TEM 200. In consequence, the axial line CX2 of the needle-shaped sample 1 when the electron microscope image is acquired by the TEM 200 is parallel to the axial line CX1 of the needle-shaped sample 1 when the base is attached to the analytical apparatus 100, and as shown in, for example, FIG. 9B, in a rotating direction RD around the axial line CX1, a position 400 into which the electron beam EB enters when the sample is set to the TEM 200 does not change after the sample is set to the analytical apparatus 100. In the present embodiment, the axial line CX2 corresponds to, for example, a first line and the axial line CX1 corresponds to, for example, a second line.

Figure 11:
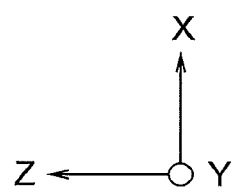
FIG. 11 is one example of a schematic view showing one example of a three-dimensional atom map prepared by the analytical apparatus shown in FIG. 1.
Figure 11:
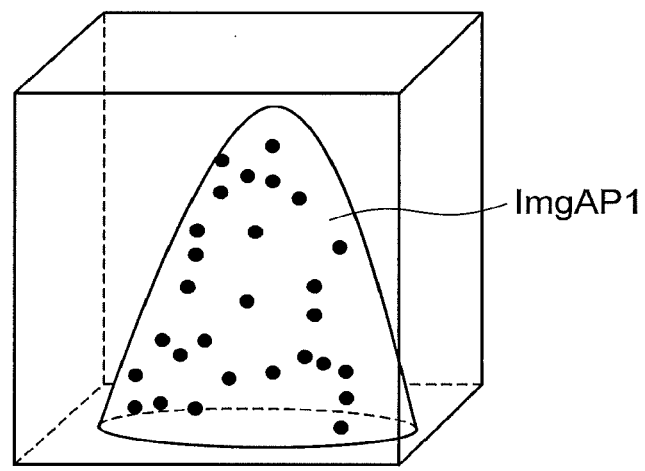
Figure 12:
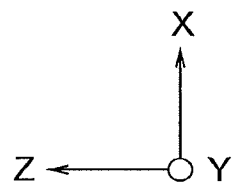
FIG. 12 is one example of a schematic view in which a crystal grain boundary is associated with the three-dimensional atom map shown in FIG. 11.
Figure 12:
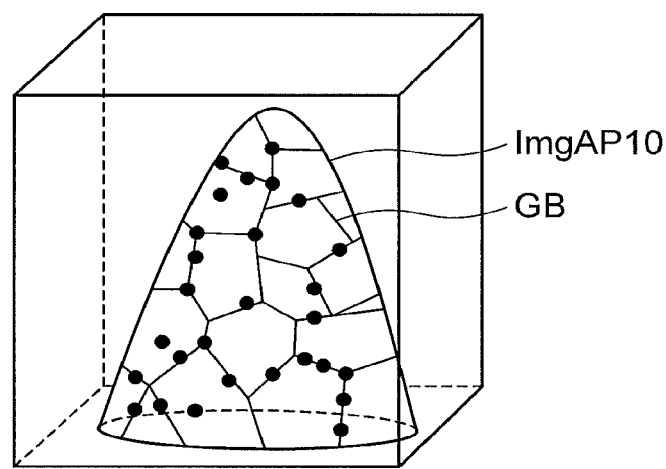

Next, the high voltage supplying section 20 applies a high voltage to the base 15 set in this manner, and the AP signal is acquired by using a voltage pulse or a laser pulse to detect the ionized atom 19, to prepare the three-dimensional atom map. FIG. 11 is a schematic view showing a three-dimensional atom map ImgAP1 as one example of the three-dimensional atom map prepared by the analytical apparatus 100.

In the present embodiment, the AP signal can be acquired from the needle-shaped sample 1 without rotating the needle-shaped sample 1 around the axial line CX1 or CX2, in accordance with the position adjustment of the base 15 by the base position adjusting section 17 and the hole shape of the base 15.

(d) Specifying of Observation Area and Sample Analysis

Next, the crystal grain boundary data of the needle-shaped sample 1 which is obtained by the TEM 200 is associated with the three-dimensional atom map prepared by using the analytical apparatus 100, by the analyzing section 80. In consequence, as shown in, for example, a schematic view of FIG. 12, a crystal grain boundary GB is associated with the three-dimensional atom map ImgAP1, and thus a three-dimensional atom map ImgAP10 is prepared in which areas of respective crystals are defined.

Next, the analyzing section 80 performs various sample analyses to the three-dimensional atom map ImgAP10 prepared as described above. In consequence, for example, it is possible to clarify grain boundary segregation of impurities or additional elements and their behaviors in crystal grains, and additionally, diffusion behaviors of the impurities or the additional elements in the crystal grains and on the crystal grain boundary can be investigated, which accurately enables an element analysis in the fine structure.

(2) Embodiment 2

In preparing a three-dimensional atom map the three-dimensional atom map might not accurately be obtained entirely or locally since, for example, a magnification of a horizontal direction and a magnification of a perpendicular direction change independently of each other to cause distortion or the like due to presence of the impurities or the additional elements in the sample, or the like.

Figure 13:
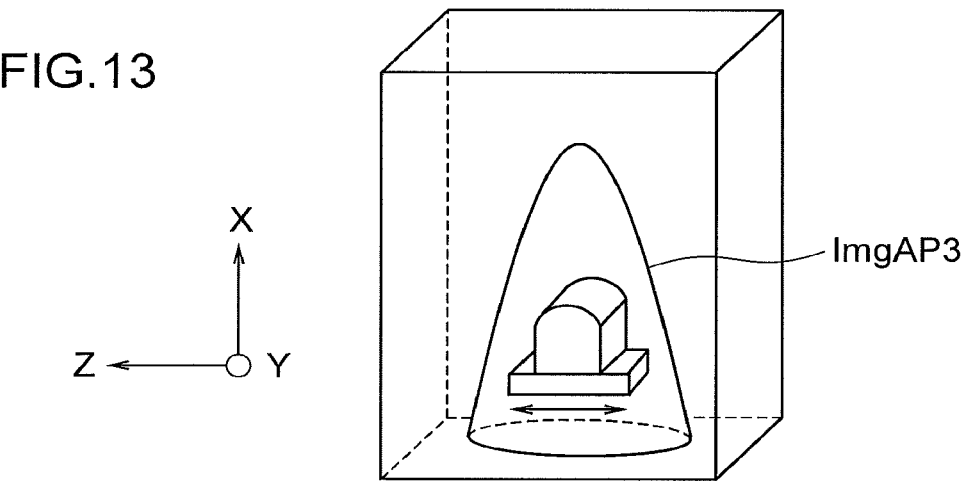
FIG. 13 is one example of a view showing one example of an accurate three-dimensional atom map in which there are not any local distortions.

FIG. 13 shows one example of the three-dimensional atom map obtained as to one example of the needle-shaped sample. An atom map ImgAP3 of FIG. 13 is one example of an accurate image in which there are no local distortions.

Figure 14:
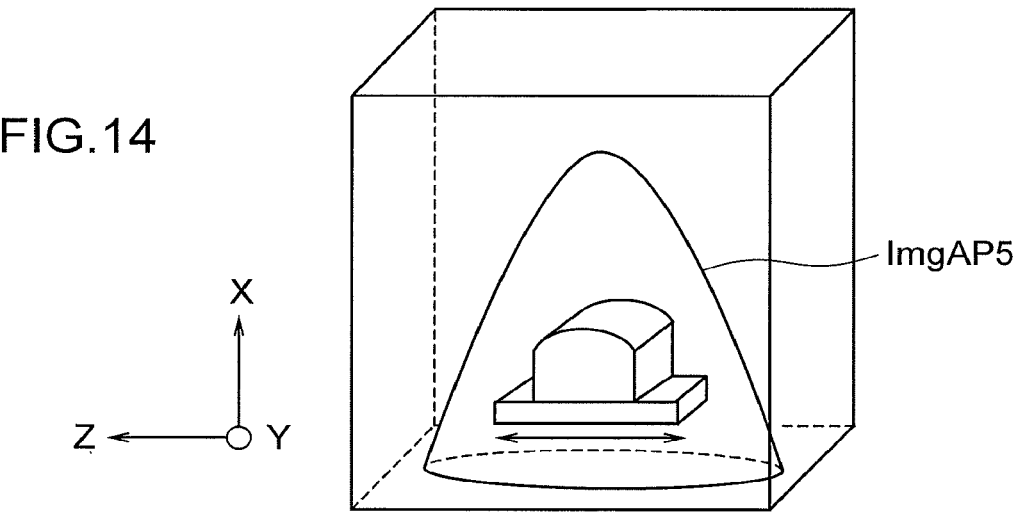
FIG. 14 is one example of a view showing one example of an inaccurate three-dimensional atom map.

FIG. 14 shows one example of the three-dimensional atom map obtained as to another example of the needle-shaped sample. An atom map ImgAP5 of FIG. 14 is one example of an inaccurate image in which a magnification of a lateral direction is larger than that of a vertical direction.

In the present embodiment, the accuracy of the three-dimensional atom map is judged prior to the sample analysis, and when it is judged that the three-dimensional atom map is not accurate, there is included a procedure of correcting the three-dimensional atom map by utilizing a signal obtained by the electron microscope.

Figure 15:
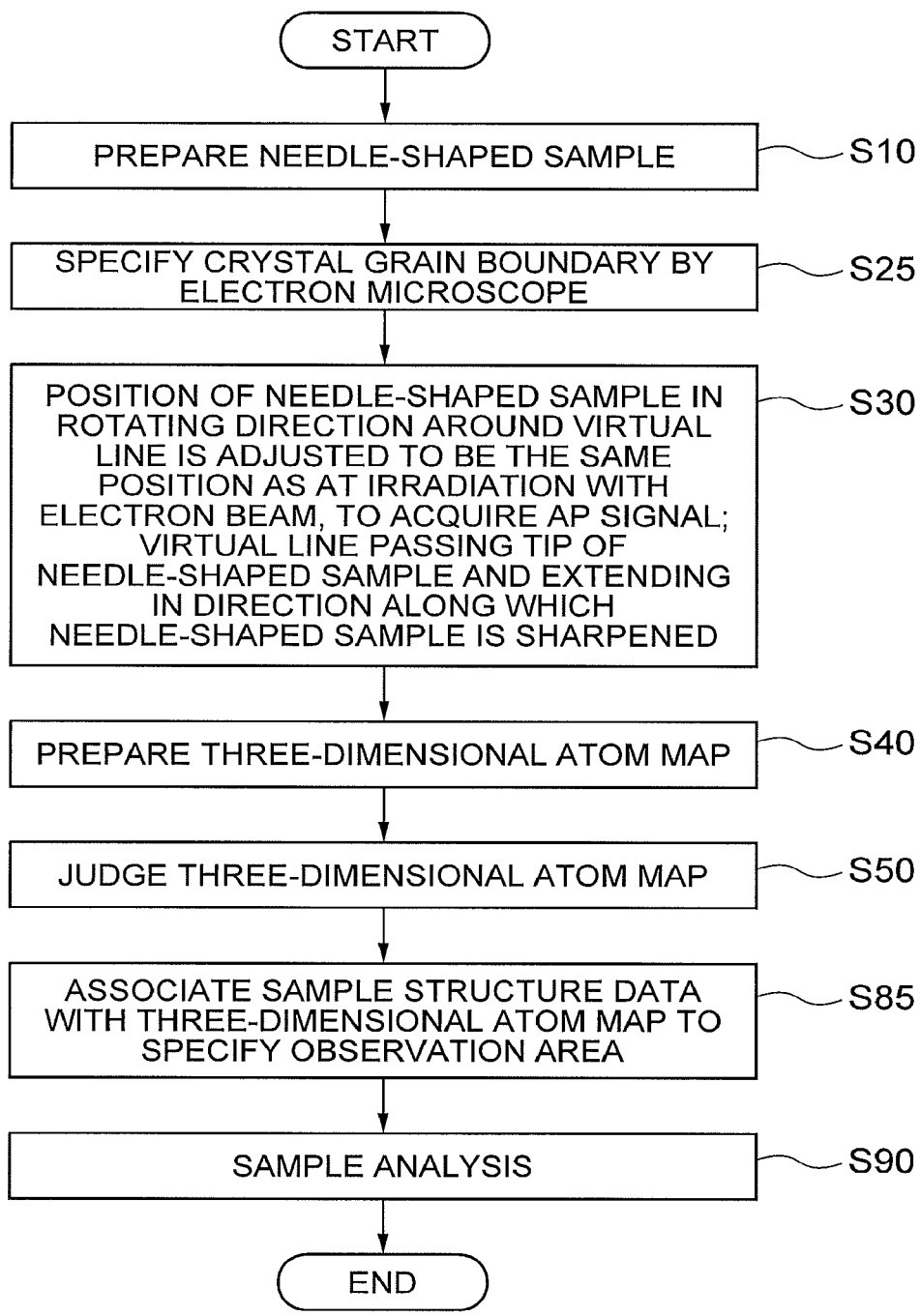
FIG. 15 is a flowchart showing a schematic procedure of an analytical method according to Embodiment 2.

FIG. 15 is a flowchart showing a schematic procedure of an analytical method according to Embodiment 2. As apparent in comparison with FIG. 7, in the analytical method of the present embodiment, the three-dimensional atom map is prepared in step S40, and then, there is included step S50 of judging the accuracy of the three-dimensional atom map before the observation area is specified in step S85.

Figure 16:
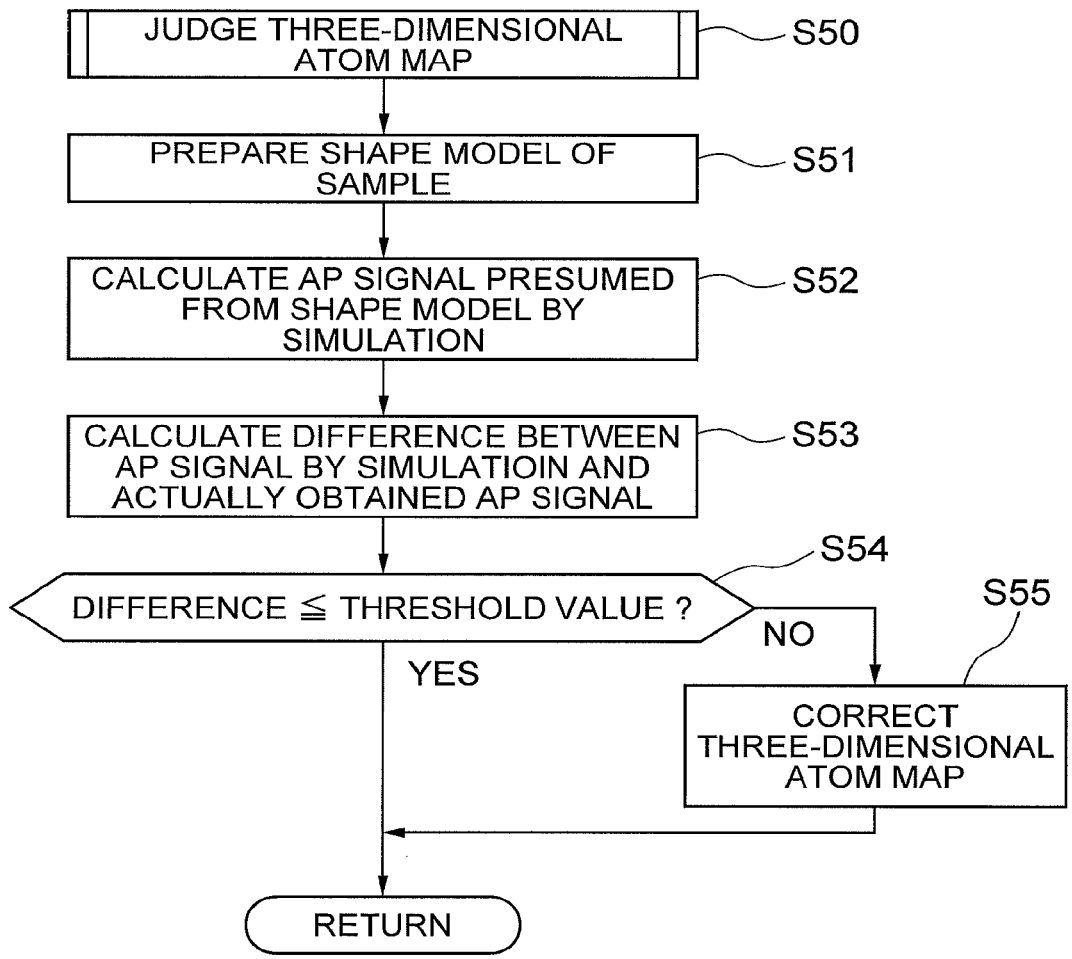
FIG. 16 is a flowchart showing a more specific procedure of a step of judging an accuracy of the three-dimensional atom map.

FIG. 16 is a flowchart showing a more specific procedure of the step S50.

First, a shape model of the needle-shaped sample 1 is prepared (step S51) by using a signal of an observation image obtained in specifying a sample structure by an electron microscope such as the TEM or the STEM (the TEM 200 in the present embodiment) (step S25 of FIG. 15). As this signal, the signal used in specifying the crystal grain boundary (the step S20 of FIG. 7) in Embodiment 1 described above may be utilized. It is to be noted that the observation image to specify the sample structure is not limited to the transmission image, and a diffraction image, an electron back scatter diffraction image, a scanning electron microscope image or an energy filter image may be used.

Subsequently, there is calculated by simulation an AP signal presumed to be obtained when the needle-shaped sample of the prepared shape model is set to the AP apparatus and a high voltage is applied to the sample to detect the ionized atom (step S52).

Next, there is calculated a difference between the AP signal (step S30 of FIG. 12) actually obtained from the needle-shaped sample 1 by the analytical apparatus 100 of FIG. 1 and the AP signal obtained by the simulation in the abovementioned step S52 (step S53).

Next, the calculated difference is compared with a predetermined threshold value (step S54). This threshold value is a value determined in accordance with a user's required specification, and indicates an accuracy of a resolution required in utilizing the three-dimensional atom map.

When the difference is the threshold value or less (YES in the step S54), it is judged that the three-dimensional atom map actually obtained from the analytical apparatus 100 is accurate, data of the sample structure is associated with the three-dimensional atom map (the step S85 of FIG. 15), and sample analysis is executed (step S90 of FIG. 15).

On the other hand, when the difference is in excess of a predetermined value (NO in the step S54), the three-dimensional atom map by the analytical apparatus 100 is corrected on the basis of the observation image of the electron microscope, or the like (step S55). Specifically, for example, the magnification of the three-dimensional atom map is corrected or local distortion in the three-dimensional atom map is corrected. In consequence, the sample analysis is performed on the basis of the corrected accurate atom map.

As mentioned above, the present embodiment includes the procedure of correcting the three-dimensional atom map when the accuracy of the three-dimensional atom map is judged and determined that the map is not accurate, and hence, the sample analysis can be performed on the basis of the more accurate three-dimensional atom map. In consequence, it is possible to more accurately perform the sample analysis, e.g., estimation of an element concentration in the fine structure, or the like.

When the shape of the hole HL of the base 15 in the cross section in the perpendicular direction to the inserting direction of the adapter 13 is a perfect circle, the needle-shaped sample 1 might rotate around the axial line during observation in the TEM 200 or the analytical apparatus 100 or during movement of the sample from the TEM 200 to the analytical apparatus 100. For example, in a case where a diameter of the needle-shaped sample 1 is 100 nm, when the sample only rotates as much as 10°, a position of the sample on a peripheral surface moves as much as 8 nm. In a case where a size of each crystal grain is of the order of several nm, the sample movement up to as much as 8 nm causes a great difficulty in associating the crystal grain boundary.

On the other hand, according to the analytical method of at least one of the abovementioned embodiments, the needle-shaped sample does not rotate around the axial line, and hence, the crystal grain boundary data can accurately be associated with the three-dimensional atom map. Accordingly, the observation area of each crystal can easily be specified on the three-dimensional atom map.

In the analytical method of Embodiment 1 or 2 described above, the TEM 200 corresponds to, for example, a first apparatus and the analytical apparatus 100 corresponds to, for example, a second apparatus. In addition, in the analytical method of Embodiment 1 or 2 described above, the image signal obtained by the imaging section 126 corresponds to, for example, a first signal and the AP signal corresponds to, for example, a second signal.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the sprit of the inventions. The accompanying claims and their equivalents are intended to cover such forms or modifications as would fall within the scope and spirit of the inventions.

The invention claimed is:

1. An analytical apparatus comprising:
a member comprising an inserting portion into which a sample holder supporting a sample is insertable and whose shape corresponds to a shape of the sample holder;
a voltage source connected to the member; and
a detector configured to detect a substance to be emitted from the sample by field evaporation,
wherein a shape of the inserting portion in a cross section of a direction perpendicular to an inserting direction of the sample holder is a shape excluding a perfect circle.

2. The apparatus of claim 1,
wherein the shape excluding the perfect circle is a shape in which a side is linked to another side to form an angle smaller than 180°.

3. The apparatus of claim 1,
wherein the shape excluding the perfect circle is a polygonal shape, an ellipse, or a circle comprising a concave portion or a convex portion.

4. The apparatus of claim 1, further comprising:
a position adjusting section configured to change a tilt of the member to an arbitrary reference surface.

5. The apparatus of claim 1, further comprising:
an analyzing section which processes a signal from the detector to prepare an atom probe image of the sample, and applies data of a grain boundary of crystals constituting the sample into the atom probe image to analyze the sample.

6. The apparatus of claim 5,
wherein the data of the crystal grain boundary is acquired by attaching the sample to an external inspection apparatus and irradiating the sample with a charged particle beam.

7. The apparatus of claim 1, further comprising:
an analyzing section which processes a signal from the detector to prepare an atom probe image of the sample, and corrects a distortion of the atom probe image on the basis of data of a structure of the sample.

8. A sample holder comprising:
a first end portion to be connected to a sample; and
a second end portion which is present on a side opposite to the first end portion and comprises a shape excluding a perfect circle.

9. The sample holder of claim 8,
wherein the shape excluding the perfect circle is a shape in which a side is linked to another side to form an angle smaller than 180°.

10. The sample holder of claim 8,
wherein the shape excluding the perfect circle is a polygonal shape, an ellipse, or a circle comprising a concave portion or a convex portion.

11. An analytical method comprising:
irradiating a sample with a charged particle beam by a first apparatus to acquire a first signal;
removing the sample from the first apparatus and attaching the sample to a second apparatus;
applying a voltage to the sample to detect a substance to be emitted from the sample, thereby acquiring a second signal; and
analyzing the sample from the first signal and the second signal,
wherein a position of the sample in a rotating direction around a first line as an axis crossing a direction in which the charged particle beam enters into the sample in the first apparatus and passing the sample is substantially the same as a position of the sample in a rotating direction around a second line as an axis parallel to the first line when the voltage is applied in the second apparatus.

12. The method of claim 11,
wherein the analyzing comprises:
preparing an image of the sample from the first signal;
specifying a grain boundary of crystals constituting the sample from the sample image;
processing the second signal to prepare a three-dimensional atom probe image of the sample; and
applying data of the specified crystal grain boundary into the three-dimensional atom probe image, and
wherein the image is a transmission image, a diffraction image, or an electron back scatter diffraction image.

13. The method of claim 11,
wherein the analyzing comprises:
preparing an image of the sample from the first signal;
specifying a structure of the sample from the sample image;
processing the second signal to prepare a three-dimensional atom probe image of the sample; and
correcting the three-dimensional atom probe image on the basis of the sample structure,
wherein the image of the sample comprises at least one of a transmission image, a diffraction image, an electron back scatter diffraction image, a scanning electron microscope image and an energy filter image.

14. The method of claim 13, further comprising:
preparing a shape model of the sample from the first signal;
calculating a second signal presumed from the shape model by simulation;
calculating a difference between the calculated second signal and the actually obtained second signal; and
comparing the difference with a threshold value,
wherein the three-dimensional atom probe image is corrected, when the difference is in excess of the threshold value.

* * * * *